United States Patent [19]

de Lange

[11] 4,341,552

[45] Jul. 27, 1982

[54] GRANULAR PESTICIDAL COMPOSITION AND METHOD OF PREPARING SAME

[75] Inventor: Willem de Lange, Weesp, Netherlands

[73] Assignee: Duphar International Research B.V., Netherlands

[21] Appl. No.: 226,442

[22] Filed: Jan. 19, 1981

Related U.S. Application Data

[63] Continuation of Ser. No. 58,214, Jul. 16, 1979, abandoned.

[30] Foreign Application Priority Data

Jul. 26, 1978 [NL] Netherlands .......................... 7807907

[51] Int. Cl.$^3$ ............................................. A01N 37/34
[52] U.S. Cl. .......................................... 71/105; 71/65; 71/79; 71/113; 71/DIG. 1
[58] Field of Search ............. 71/105, DIG. 1; 424/31, 424/23

[56] References Cited

U.S. PATENT DOCUMENTS

| | | | |
|---|---|---|---|
| Re. 25,205 | 7/1962 | Feinstone | 424/31 |
| 2,500,770 | 3/1950 | Pierce | 71/DIG. 1 |
| 3,094,464 | 6/1963 | Joullie et al. | 424/31 |
| 3,137,618 | 6/1964 | Pearce | 71/DIG. 1 |
| 3,382,150 | 5/1968 | Grass, Jr. et al. | 424/31 |
| 3,497,345 | 2/1970 | Duyfjes | 71/105 |
| 3,617,246 | 11/1971 | Duyfjes et al. | 71/105 |
| 3,725,031 | 4/1973 | Balassa | 71/DIG. 1 |
| 3,785,798 | 1/1974 | Horai et al. | 71/DIG. 1 |
| 4,136,250 | 1/1979 | Mueller et al. | 71/DIG. 1 |

FOREIGN PATENT DOCUMENTS

| | | | |
|---|---|---|---|
| 36-10850 | 6/1961 | Japan | 71/DIG. 1 |
| 728759 | 4/1955 | United Kingdom | 424/31 |
| 1233418 | 5/1971 | United Kingdom | 71/DIG. 1 |

*Primary Examiner*—Glennon H. Hollrah
*Attorney, Agent, or Firm*—Stevens, Davis, Miller & Mosher

[57] ABSTRACT

The invention relates to a granular pesticidal composition the core of which is surrounded by a layer containing silicon dioxide which is silanated at the surface; the composition contains preferably from 0.05 to 5% by weight of silanated silicon dioxide.

7 Claims, No Drawings

GRANULAR PESTICIDAL COMPOSITION AND METHOD OF PREPARING SAME

This is a continuation of application Ser. No. 058,214, filed July 16, 1979, now abandoned.

The invention relates to a granular pesticidal composition in which the core of the granules comprises the following ingredients: (a) one or more active compounds of which at least one has a comparatively high vapor pressure, (b) a solid inert carrier, (c) one or more binders, and (d), if desired, surface-active substances, lubricants, stabilisers and/or other suitable additives. The invention furthermore relates to a method of preparing such a composition, as well as to a method of controlling and/or preventing noxious organisms.

In granular pesticidal compositions comprising as the active compound or as one of the active compounds a substance having a comparatively high vapor pressure, it occurs that crystals of the comparatively volatile compounds deposit on the surface of the granules upon storage; these crystals may agglomerate to form floccules: resulting in the formation of crystal wool. Substances having a comparatively high vapor pressure are to be understood to mean herein compounds the steam distillation constant of which exceeds 1, for example, the herbicide 2,6-dichlorobenzonitrile. This constant can be determined as described by Schoorl, Organische Analyse, Amsterdam 1937, Vol. II, pp. 195–197. For 2,6-dichlorobenzonitrile this value is 20.6±0.7 as has been found by applicants. This crystal wool formation has several disadvantages.

For example, such a composition containing crystal wool makes a less favourable impression on the user. However, more serious disadvantages present themselves upon handling the composition. The crystal wool is loose on the granules and easily detaches when the composition is repacked or scattered; as a result of the low weight of the crystal wool, it can easily start dusting so that it can deposit on the body of the user or can be inhaled by the user. Another important disadvantage is that the light crystal wool is very easily blown away to an adjacent plot on which there may be a crop which is sensitive to the pesticide in question. When such a composition is repacked or scattered, the crystal wool can also easily land in adjacent surface water and possibly damage the living organisms therein.

U.S. Pat. No. 3,725,031 relates to a herbicidal composition consisting of an inert porous carrier and a volatile herbicide. It is suggested that certain resinous and/or waxy materials be added to said composition so as to counteract loss of the herbicide, inter alia, by evaporation, and thus extend the effective life of the composition. The active substance is mixed with the resinous or waxy material, after which the mixture is absorbed on a suitable porous carrier. Obviously the activity of the added material is based on reducing the evaporation by reducing the surface area of the volatile herbicide.

It has now been found that the above-mentioned formation of crystal wool during storage of pesticidal granules can be reduced and/or prevented by embedding the core of a pesticidal granule in a layer containing silicon dioxide which is silanated at the surface.

The expression "silanated" is to be understood to mean herein a treatment with a silane, for example an alkyltrichlorosilane, a dialkyldichlorosilane or a trialkylchlorosilane. As a result of this the surface of the, usually synthetic, silicon dioxide is provided with Si(R)$_n$ groups and the silicon dioxide becomes hydrophobic. A typical example of such a silanated silicon dioxide is Aerosil R 972 obtained by a surface treatment of pure silicon dioxide, obtained by flame hydrolysis, with dimethyl-dichlorosilane; it is assumed that groups of the following structure

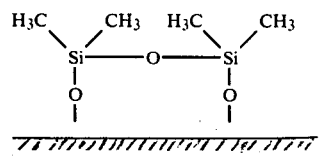

are present at the surface of Aerosil R 972.

Such a "dry" after-treatment is very simple to perform, the more so since the granules are usually after-treated with one or more pigments and/or dyes, as described in applicants' Netherlands patent specification No. 149989 corresponding to U.S. Pat. No. 3,497,345, the contents of which are hereby incorporated by reference; in this patent specification titanium dioxide is used as a pigment. Pigmentation and provision of silanated silicon dioxide can then take place collectively in one after-treatment. This after-treatment is simple and cheap as compared with the pre-treatment of the active substance with waxy or resinous material disclosed in U.S. Pat. No. 3,725,031. In addition, the carrier to be used according to the above-mentioned U.S. patent specification is restricted to porous granules, whereas the after-treatment according to the present invention is particularly suitable for compositions on the basis of non-porous carriers. As non-porous carriers are to be considered mineral materials which can absorb less than 5% water, for example, finely ground minerals of the calcium-, magnesium- or magnesium-calcium carbonate type, for example, dolomite.

Granules having one of these materials as a carrier are preferably prepared according to a method disclosed in applicants' Netherlands patent specification No. 150660 corresponding to U.S. Pat. No. 3,167,246, the contents of which are hereby incorporated by reference.

The invention is the more surprising because, as will become apparent from the examples, such an effect is not obtained when untreated silicon dioxide, for example, Zeosil 39 or Aerosil 200 is used instead of silanated silicon dioxide. Other hydrophobated materials, for example, Omya B.S.H., do not give a sufficiently favourable result either. Omya B.S.H. is chalk the particles of which have been subjected to a surface treatment with stearin vapour.

It has been found in practice that good results are obtained when a composition embodying the invention contains from 0.05–5% by weight of silanated silicon dioxide.

According to a further aspect of the invention there is also provided a method of controlling and/or preventing noxious organisms, in which the infected area and/or the area to be protected is treated with the composition in a quantity corresponding to 0.5 to 100 kgs of active substance(s) per hectare.

The invention will now be described in greater detail with reference to the following examples.

EXAMPLE 1

A granular composition containing 6.75% by weight of 2,6-dichlorobenzonitrile and 10% by weight of sodium α,α-dichloropropionate as active substances and 5% by weight of lignin sulfonates as a binder with dolomite as a carrier was after-treated with the additions recorded in the table according to the method described in Netherlands patent specification No. 149989.* The compositions thus treated were then stored for a given period of time at the indicated temperature, after which the formation of crystal wool, if any, was established under the microscope. This wool formation is indicated by the so-called wool code, an arbitrary standard from 0 to 5 having the following meanings:

0 = no crystal wool
½ = hardly any crystal wool
≦1 = product acceptable for practice
>1 = no longer acceptable
5 = bad composition; much crystal wool-visible with the naked eye.

*corresponding with U.S. Pat. No. 3,497,345.

The following results were obtained.

| Formulation | Addition(s) | Quantity in % by weight | wool code after storage at ... °C. for ... days | | | | | | | | | |
|---|---|---|---|---|---|---|---|---|---|---|---|---|
| | | | storage at 54° C. | | | storage at room temperature | | | | | | |
| | | | 1 | 3 | 7 | 1 | 3 | 7 | 14 | 30 | 60 | 120 |
| a | nil | — | 1¼ | 3 | 3½ | ½ | | 1¼ | 2 | 3½ | 3 | 3 |
| b | Aerosil R 972 | 0.5 | <¼ | 0 | | | | 0 | 0 | <¼ | <¼ | ¼ |
| c | Aerosil 200 | 0.5 | 2 | 2½ | | | | ¾ | 1½ | 2½ | 3 | 3 |
| d | Zeosil 39 | 0.5 | 2 | 2 | | | | 1¼ | 1¼ | 1½ | 2 | 3 |
| e | Aerosil R 972 | 1.0 | 0 | <¼ | | | | 0 | 0 | 0 | ¼ | <¼ |
| f | Zeosil 39 | 1.0 | 1¼ | 1½ | | | | ½ | 1¼ | 1½ | 1½ | 1¾ |
| g | Omya B.S.H. | 0.5 | 1½ | 2¼ | 2½ | | | ½ | ¾ | 1½ | 2 | 3 |
| h | Omya B.S.H. | 1.0 | 1¼ | 2¼ | 3 | | | ¼ | ¼ | 1¾ | 1¾ | 2½ |
| i | TiO₂ | 0.5 | 1½ | 2¾ | 3 | 0 | | | | 2 | 1¾ | 2¼ |
| j | Aerosil R 972 + TiO₂ | 0.35 + 0.15 | 0 | ¼ | ½ | <¼ | | <¼ | ¼ | ¼ | ¼ | ¼ |
| k | Aerosil R 972 + TiO₂ | 0.45 + 0.05 | 0 | <¼ | ¼ | 0 | | 0 | 0 | <¼ | <¼ | <¼ |

EXAMPLE 2

The wool code of compositions containing 6.75% by weight of 2,6-dichlorobenzonitrile as the active substance and 5% by weight of lignin sulphonates as a binder with dolomite as a carrier was determined in a manner corresponding to that of example 1. The results are recorded in the following table:

| formulation | addition(s) | quantity in % by weight | wool code after storage at ... °C. for ... days | | | | | | | | |
|---|---|---|---|---|---|---|---|---|---|---|---|
| | | | storage at 54° C. | | | | storage at room temperature | | | | |
| | | | 3 | 7 | 14 | 30 | 7 | 14 | 30 | 60 | 120 |
| l | nil | — | 1 | 1½ | 1½ | 1¾ | ¼ | ¼ | 1 | 1½ | 1¼ |
| m | Aerosil R 972 | 0.5 | <¼ | <¼ | <¼ | ¼ | 0 | 0 | 0 | <¼ | 0 |
| n | TiO₂ | 0.75 | ¼ | ¾ | ¾ | 1 | 0 | 0 | <¼ | <¼ | <¼ |
| o | Aerosil R 972 + TiO₂ | 0.37 + 0.37 | <¼ | <¼ | <¼ | ¼ | 0 | 0 | 0 | 0 | 0 |

What is claimed is:

1. A granular pesticidal composition wherein each granule comprises:
    (A) a core comprising a herbicidally effective amount of a herbicide having a steam distillation constant in excess of 1 and a finely divided solid inert carrier for said herbicide, and
    (B) a layer surrounding said core, said layer comprising silicon dioxide, the particles of which are provided with mono-, di-, and/or trialkylsilyl groups at their surface.

2. The herbicidal composition of claim 1 wherein said herbicide is 2,6-dichlorobenzonitrile.

3. The herbicidal composition of claim 1 wherein said inert carrier is a material capable of absorbing less than 5% of water.

4. A composition as claimed in claim 3, characterized in that the carrier is a finely ground mineral consisting essentially of calcium- magnesium- or magnesium-calcium carbonate type.

5. A composition as claimed in claim 1, characterized in that the composition contains from 0.05 to 5% by weight of silanated silicon dioxide.

6. The herbicidal composition of claim 5 wherein said herbicide is 2,6-dichlorobenzonitrile.

7. A composition as claimed in claim 1, characterized in that the layer surrounding the core of the granules also comprises a visually effective amount of titanium dioxide as a pigment.

* * * * *